US006788411B1

(12) United States Patent
Lebens

(10) Patent No.: US 6,788,411 B1
(45) Date of Patent: Sep. 7, 2004

(54) METHOD AND APPARATUS FOR ADJUSTING ILLUMINATION ANGLE

(75) Inventor: Gary A. Lebens, Chaska, MN (US)

(73) Assignee: PPT Vision, Inc., Eden Prairie, MN (US)

( * ) Notice: Subject to any disclaimer, the term of this patent is extended or adjusted under 35 U.S.C. 154(b) by 672 days.

(21) Appl. No.: 09/612,763

(22) Filed: Jul. 10, 2000

Related U.S. Application Data

(60) Provisional application No. 60/142,999, filed on Jul. 8, 1999.

(51) Int. Cl.[7] ............................................. G01B 11/00
(52) U.S. Cl. ....................... 356/394; 356/369; 356/364; 382/141
(58) Field of Search ................................ 356/394, 364, 356/369; 382/141–150

(56) References Cited

U.S. PATENT DOCUMENTS

| | | | |
|---|---|---|---|
| 4,208,579 A | 6/1980 | Scrivo et al. ............... | 250/227 |
| 4,212,073 A | 7/1980 | Balasubramanian ........ | 364/562 |
| 4,290,095 A | 9/1981 | Schmidt ..................... | 362/191 |
| 4,346,329 A | 8/1982 | Schmidt ..................... | 315/51 |
| 4,509,266 A | 4/1985 | Cusack ...................... | 33/174 L |
| 4,592,147 A | 6/1986 | Herman ....................... | 33/366 |
| 4,639,139 A | 1/1987 | Wyant et al. ............... | 356/359 |
| 4,641,972 A | 2/1987 | Halioua et al. ............. | 356/376 |
| 4,820,229 A | 4/1989 | Spraggins ................... | 446/26 |
| 4,831,504 A | 5/1989 | Nishizawa et al. ......... | 362/100 |
| 4,882,498 A | 11/1989 | Cochran et al. ............ | 350/571 |
| 4,893,815 A | 1/1990 | Rowan ........................ | 273/84 |
| 4,914,289 A | 4/1990 | Nguyen et al. .......... | 250/223 B |
| 4,962,347 A | 10/1990 | Burroughs et al. ........... | 320/48 |
| 4,964,023 A | 10/1990 | Nishizawa et al. ......... | 362/100 |
| 4,965,665 A | 10/1990 | Amir .......................... | 358/101 |
| 4,967,284 A | 10/1990 | Yoshida et al. ............. | 358/300 |
| 4,972,093 A | 11/1990 | Cochran et al. ............ | 250/572 |
| 4,974,138 A | 11/1990 | Negishi ....................... | 362/347 |
| 4,978,857 A | 12/1990 | Juengel ....................... | 250/551 |
| 5,010,412 A | 4/1991 | Garriss ....................... | 358/240 |

(List continued on next page.)

FOREIGN PATENT DOCUMENTS

| | | | | |
|---|---|---|---|---|
| EP | 0638801 | 2/1995 | .......... | G01N/21/88 |
| WO | 98/02716 | 1/1998 | ........... | G01B/11/03 |

OTHER PUBLICATIONS

"About Boulder Nonlinear Systems", *Boulder Nonlinear Systems, Inc.*, http://www.bnonlinear.com/AboutBNS.htm, pp. 1–4, (2000).

(List continued on next page.)

*Primary Examiner*—Frank G. Font
*Assistant Examiner*—Roy M. Punnoose
(74) *Attorney, Agent, or Firm*—Schwegman, Lundberg, Woessner & Kluth, P.A.

(57) ABSTRACT

In a machine-vision system for inspecting a part or either object, the invention provides a method and apparatus providing illumination with high-speed changing and/or automatic adjustment of not only the illumination's angle, but also the dispersion, intensity, and/or color. Optionally, a light source emits polarized light, a machine-vision imager obtains an image, and a processor receives the image and generates a quality parameter based on the image. One or more of the various means described selectively direct the light in a predetermined pattern based on its polarization and based on the quality parameter of the image. A machine-vision method includes setting one or more illumination parameters, illuminating the object based on the one or more illumination parameters, obtaining an image of the illuminated object, generating a quality parameter based on an image quality of a predetermined region of interest in the image, and iterating using a different illumination parameter.

21 Claims, 4 Drawing Sheets

U.S. PATENT DOCUMENTS

| | | |
|---|---|---|
| 5,015,918 A | 5/1991 | Copeland ................... 315/76 |
| 5,051,825 A | 9/1991 | Cochran et al. ............ 358/106 |
| 5,060,065 A | 10/1991 | Wasserman ................ 358/106 |
| 5,065,035 A | 11/1991 | Juengel ..................... 250/551 |
| 5,072,127 A | 12/1991 | Cochran et al. ............ 250/572 |
| 5,085,502 A | 2/1992 | Womack et al. ............ 356/376 |
| 5,172,005 A | 12/1992 | Cochran et al. ............. 250/57 |
| 5,179,335 A | 1/1993 | Nor ............................ 320/21 |
| 5,179,474 A | 1/1993 | Bailey et al. ............... 359/798 |
| 5,279,513 A | 1/1994 | Connelly ................... 446/219 |
| 5,299,227 A | 3/1994 | Rose ............................ 375/1 |
| 5,355,221 A | 10/1994 | Cohen et al. ............... 356/359 |
| 5,398,113 A | 3/1995 | de Groot ................... 356/360 |
| 5,424,927 A | 6/1995 | Schaller et al. ............ 362/157 |
| 5,457,492 A | 10/1995 | Sasaki et al. ............... 348/126 |
| 5,465,152 A | 11/1995 | Bilodeau et al. ........... 356/371 |
| 5,546,189 A | 8/1996 | Svetkoff et al. ............ 356/376 |
| 5,561,525 A | 10/1996 | Toyonaga et al. .......... 356/360 |
| 5,636,025 A | 6/1997 | Bieman et al. ............. 356/374 |
| 5,646,733 A | 7/1997 | Bieman ...................... 356/376 |
| 5,680,215 A | 10/1997 | Huber et al. ................ 356/371 |
| 5,745,176 A | 4/1998 | Lebens ....................... 348/370 |
| 5,825,495 A | 10/1998 | Huber ........................ 356/371 |
| 5,828,449 A | 10/1998 | King et al. ................. 356/237 |
| 5,838,247 A | 11/1998 | Bladowski ............ 340/815.45 |
| 5,890,794 A | 4/1999 | Abtahi et al. ............... 362/294 |
| 6,084,631 A | 7/2000 | Tonkin et al. .............. 248/212 |
| 6,095,661 A | 8/2000 | Lebens et al. .............. 362/184 |
| 6,263,099 B1 * | 7/2001 | Maeda et al. ............... 382/149 |

OTHER PUBLICATIONS

Bains, S., "Advance said to hold promise for wavelength–division multiplexing—Device steers white light through wide angles", *EE Times,* Issue 1060; Section: Technology; http://www.techweb.com/se/directlink.cgi?EET19990510S0046, 4 pages, (May 10, 1999).

Bains, S., "Device steers white light through wide angles", *EE Times,* pp. 1–2, (1999).

Ballard, D.H., "Generalizing the Hough Transform to Detect Arbitrary Shapes", *Pattern Recognition, 13*(2), Pergamon Press, pp. 183–194, (1981).

Davies, E.R., *Machine Vision: Theory, Algorithms, Practicalities, 2nd Edition,* Academic Press, San Diego, pp. 195–210, (1997).

Uber, G.T., "Illumination Methods for Machine Vision", *SPIE vol. 728, Optics, Illumination, and Image Sensing for Machine Vision,* pp. 93–102, (1986).

Yang, H.S., et al., "Determination of the Identity, Position and Orientation of the Topmost Object in a Pile: Some Further Experiments", *IEEE International Conference on Robotics and Automation, 1,* San Francisco. CA, 293–298, (1986).

* cited by examiner

METHOD AND APPARATUS FOR ADJUSTING ILLUMINATION ANGLE

This application claims benefit of Ser. No. 60/142,999 filed Jul. 8, 1999.

FIELD OF THE INVENTION

The present invention generally concerns machine-vision, particularly systems and methods for lighting/illuminating objects in machine-vision systems.

COPYRIGHT NOTICE/PERMISSION

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever. The following notice applies to the software and data as described below and in the drawings hereto: Copyright © 1998–2000, PPT Vision, Inc., All Rights Reserved.

RELATED APPLICATIONS

This invention is related to:

U.S. Pat. No. 6,603,103, entitled "CIRCUIT FOR MACHINE-VISION SYSTEM",

U.S. patent application Ser. No. 09/350,050, entitled "MACHINE-VISION SYSTEM AND METHOD FOR RANDOMLY LOCATED PARTS" (now abandoned), filed Jul. 8, 1999, U.S. patent application Ser. No. 09/350,255, entitled "PARTS MANIPULATION AND INSPECTION SYSTEM AND METHOD" (now abandoned), filed Jul. 8, 1999, U.S. patent application Ser. No. 09/349,684, entitled "MACHINE-VISION SYSTEMS AND METHODS WITH UP AND DOWN LIGHTS" (now abandoned), filed Jul. 8, 1999, U.S. patent application Ser. No. 09/349,948, entitled "METHOD AND APPARATUS TO CALCULATE BGA BALL TOPS" (now abandoned), filed Jul. 8, 1999, U.S. Pat. No. 6,522,777, entitled "COMBINED 3D AND 2D-SCANNING MACHINE-VISION SYSTEM AND METHOD"

U.S. patent application Ser. No. 09/350,037, entitled "MACHINE-VISION SYSTEM AND METHOD HAVING A SINE-WAVE PROJECTION PATTERN" (now abandoned), filed Jul. 8, 1999, U.S. patent application Ser. No. 09/350,251, entitled "TRAY FLIPPER AND METHOD FOR PARTS INSPECTION" (filed Jul. 8, 1999, U.S. Pat. No. 6,509,559, entitled "BINARY GRATING AND METHOD FOR GENERATING A MOIRE PATTERN FOR 3D IMAGING"

U.S. Pat. No. 6,486,963, entitled "PRECISION 3D SCANNER BASE AND METHOD FOR MEASURING MANUFACTURED PARTS"

U.S. Pat. No. 6,501,554, entitled "3D SCANNER AND METHOD FOR MEASURING HEIGHTS AND ANGLES OF MANUFACTURED PARTS"

which are all assigned to a common assignee, and which are incorporated herein by reference.

BACKGROUND OF THE INVENTION

There is a widespread need for inspection data for electronic parts in a manufacturing environment. Machine-vision systems have become vital to many complex manufacturing processes, particularly for quality control. For example, during the manufacture of integrated circuits which contain millions of transistors and other electrical components, machine-vision systems visually inspect the circuits at various manufacturing stages for surface blemishes or other defects, rejecting or accepting circuits based on appearance.

Machine-vision systems typically includes an imaging device, such as an electronic camera and an illumination system, which illuminates an object for the camera. The typical illumination system, generally designed to illuminate all sides of an object simultaneously, comprises some form of a circular ring of lights, for example a ring-shaped flashtube, a ring of light-emitting diodes, or a ring of optical fibers. The circular ring of lights usually lies between the camera and object, with the camera looking down through the ring to the object and the lights oriented down and inward to the object.

Conventional illumination systems suffer from at least two major problems. First, they lack a convenient way for varying the angle of illumination, that is, the angle light strikes an object. Conventional illumination systems require technicians to manually adjust orientation of the complete ring of lights or to manually adjust orientation of its individual lights. However, manual adjustments are not only time consuming, but often lead to angular variations which compromise consistency of machine-vision systems. Second, conventional systems lack convenient way of switching from one illumination mode to another, for example, from a particular selected angle of illumination to a multi-directional object illumination, such as "cloudy-day illumination." Some select-angle illumination modes are better for viewing scratches, while cloudy-day illumination is better for specular or irregular surfaces. This lack of a convenient way of switching illumination modes often leads to use of more than one machine-vision system, and thus forces manufacturers to buy separate systems, to use human inspectors, or to skip inspection for some types of defects. Accordingly, there is a need for better illumination systems for machine-vision systems.

SUMMARY OF THE INVENTION

In the context of a machine-vision system for inspecting a part, this invention includes method and apparatus to provide high-speed changing and/or automatic adjustment of illumination angle, dispersion, intensity, and/or color of illumination in a machine vision system.

One aspect of the present invention provides a machine-vision system having an optical axis. This system includes a light source emitting light having a polarization, a machine-vision imager that obtains an image of an object illuminated by the light, a processor coupled to receive an image from the imager, and operative to generate a quality parameter based on the image, and one or more of the various means as described above for selectively directing the light in a predetermined pattern based on its polarization and based on the quality parameter of the image.

Another aspect of the present invention provides a machine-vision system having an optical axis. This system includes a machine-vision imager located along the optical axis, a controllable light source, a first optical element that selectively directs light in a first predetermined pattern relative to the optical axis based on light characteristics, a second optical element, that directs light in a second predetermined pattern relative to the optical axis, and an electronic controller operatively coupled to the imager and the controllable light source to control the light characteristics and thereby selecting one or more of the first and second predetermined patterns.

Another aspect of the present invention provides an illumination method that includes emitting light, selectively polarizing the light, and selectively directing the light based on its polarization.

In some embodiments, the selectively directing provides two or more different angles of illumination (e.g., alpha and/or beta). In some such embodiments, the angle is a conical angle of a ring illumination.

Yet another aspect of the present invention provides a machine-vision method for inspecting an object. This method includes (a) setting one or more illumination parameters, (b) illuminating the object based on the one or more illumination parameters, (c) obtaining an image of the illuminated object, (d) generating a quality parameter based on an image quality of a predetermined region of interest in the image, and (e) iterating (b), (c), and (d) using a different illumination parameter. In some embodiments of this method, the iterating is based on the quality parameter. In some embodiments, the one or more illumination parameters includes a predetermined azimuth angle of illumination. In some embodiments, the one or more illumination parameters includes a predetermined compass angle of illumination. In some embodiments, the one or more illumination parameters includes a predetermined compass angle of illumination.

DETAILED DESCRIPTION OF THE PREFERRED EMBODIMENT

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Machine-vision and optical-feature-recognition techniques can be used to distinguish parts that deviate from a predetermined intended aspect of an ideal device. In this description, a "device" is meant to be any part, device of manufacture or object, for example an integrated circuit package, electronic part, semiconductor, molded plastic part, aluminum wheel, gemstone or even an egg or strawberry, which can be inspected. Typically, according to the present invention, a manufacturing operation will use geometric information about the parts acquired from machine-vision inspection of the device to distinguish "good" devices from "bad" devices, and can discard the bad devices and insert previously inspected good devices in their place, for example to obtain a tray of all-good devices. In some embodiments, the devices under test are placed into pocketed trays or into cartons for ease of handling and transport, and inspection will take place of the devices while the devices are in the pocketed trays, according to the present invention. In other embodiments, a parts holder having a clamping mechanism is used to hold a plurality of parts, such as disk suspensions, to an inspection-station fixture.

Figure 1:
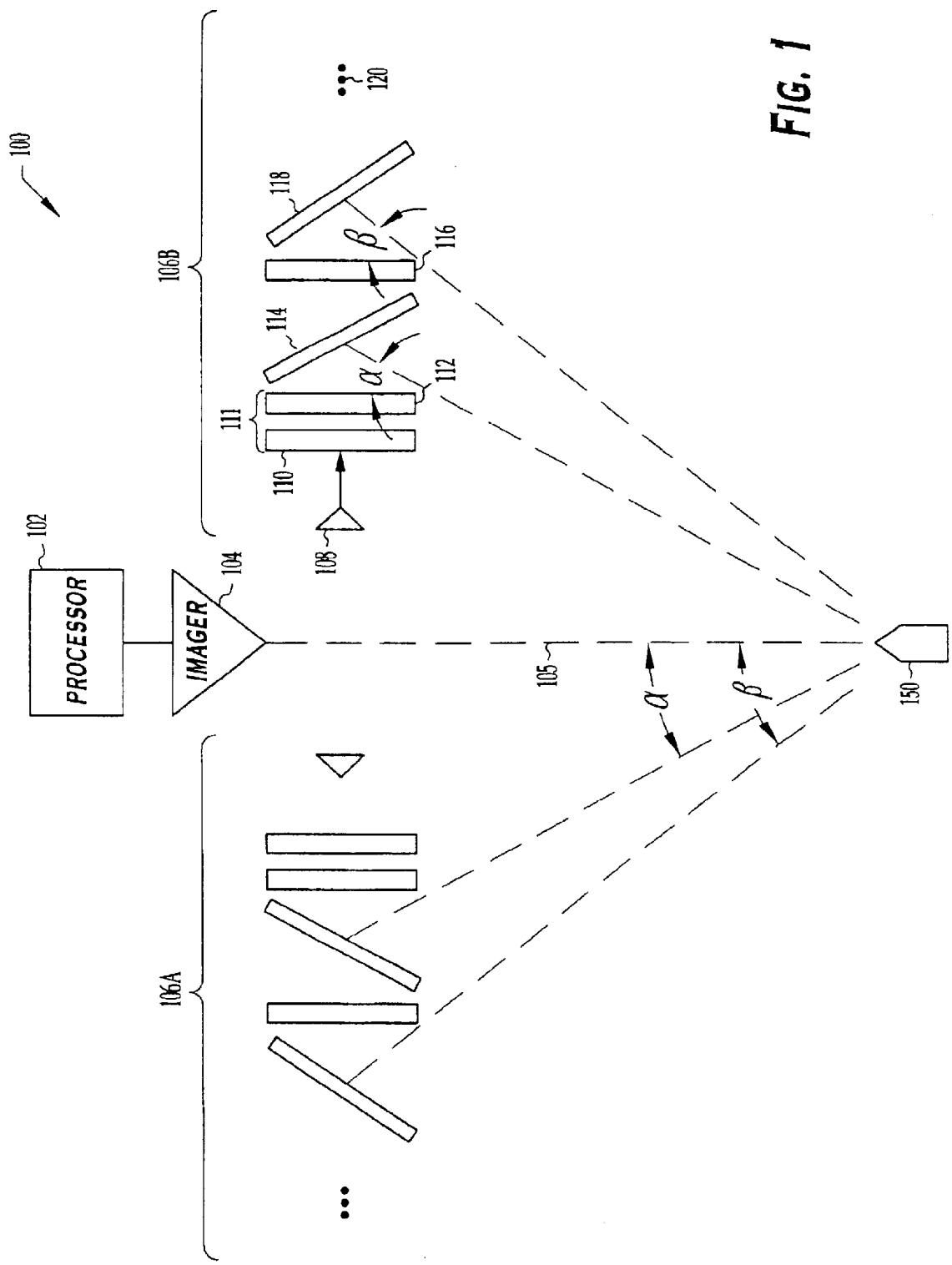
FIG. 1 shows a cross-section side-view schematic of an embodiment of the present invention, an electronically-controlled variable-angle machine-vision illumination system 100.

FIG. 1 shows a cross-sectional block diagram of an exemplary machine-vision system 100 embodying teachings and principles of the present invention. System 100 includes an analog or digital processor 102, an analog or digital imager 104 having an optical axis 105, and a symmetric illumination system 106 (including left and right halves 106a and 106b) that illuminates object 150 at selectable angles α and β relative to axis 105. Each half (106a and 106b) of illumination system 106 includes a light source 108, a polarizer 110, a first liquid-crystal panel 112, a first polarized reflector 114, a second liquid-crystal panel 116, and a second polarized reflector 118. (The ellipsis 120 indicates that the exemplary embodiment includes further liquid-crystal panels and corresponding polarized reflectors.)

In operation, light source 108 emits light to polarizer 110, which polarizes the light in a select direction. Polarized light exits to liquid-crystal panel 112 which may or may not alter the polarization of the polarized light, depending on applied electrical stimulus. Light exiting panel 112 is reflected by or transmitted through polarized reflector 114 depending on its polarization. Reflector 114 is oriented to reflect appropriately polarized light toward object 150 at a first predetermined angle a relative to axis 105.

Light that is not polarized for reflection by reflector 114 passes to second liquid-crystal panel 116 which with appropriate electrical stimulus changes polarization of incoming light. Light exiting panel 116 strikes polarized reflector 118, which reflects or transmits it, based on its polarization. Reflector 118 is oriented to reflect appropriately polarized light toward object 150 at a second predetermined angle β relative to axis 105.

Thus, using a light source, and one or more sets of electrically controllable polarizers and polarized reflectors, one can select various angles of illumination for objects in a machine-vision system. Thus, without physically changing optical components, one can quickly and easily change the illumination angle to obtain images that improve contrast and/or clarity of features of interest on object 150. In some cases, highly reflective or specular features can be better imaged if the light is at a particular angle that either enhances or suppresses reflections from such surfaces to the camera 104. In other cases, fine machining marks (e.g., polishing lines) will show clearly if the light is at a particular angle, and depending on whether the user wants to enhance or suppress such marks on the image, a different angle will be chosen.

In some embodiments, optical element 110 and optical element 112 together combine to form an electrically controllable polarizer 111, wherein the angle of polarization can be electronically controlled by processor 102. Thus, if controllable polarizer 111 sets a first angle of polarization that matches that which is reflected by polarized reflector 114, then illumination angle alpha (α) is obtained. On the other hand, if the angle of polarization generated by controllable polarizer 111 matches that which is transmitted by polarized reflector 114, then, in some embodiments (i.e., those that omit LCD 116 and have reflector 118 totally reflecting), the transmitted light is reflected by reflector 118 with illumination angle beta (β). In other embodiments that include LCD 116, the polarizer 110, LCD 114 and LCD 116 together form an electronically controllable polarizer for the light directed to reflector 118 (and optionally further elements 120).

In some embodiments, illumination source 106 is circularly symmetric, having a ring light source 108, a ring polarizer 110, a ring liquid-crystal device (LCD) 112, a conical section angled polarized reflector/transmitter 114, a second ring LCD 116, and a second conical section angled polarized reflector/transmitter 114. In some embodiments, further pairs of LCDs and angled reflectors (shown as ellipses 120) are included. In some embodiments, LCD 116 is omitted for the outermost ring, and reflector 118 is maximally reflective for all incident light. In other embodiments, further polarizers 116 and reflectors 118 are included to provide yet other angles of illumination light. In some embodiments, each ring or conical section is centered about optical axis 105. In such embodiments, selectable illumination angles α and β are conical angles relative to the optical axis 105 that represent the conical surface that the illumination is centered about. In some such embodiments, light source 108 is one or more rows of light-emitting diodes (LEDs) mounted facing radially outward on a cylindrical surface. In some embodiments, the LEDs of light source 108 are divided into banks, wherein each bank is separately driven (e.g., eight banks, wherein each bank represents a forty-five-degree section of the ring, for example the eight compass directions N, NE, E, SE, S, SW, W, and NW—wherein compass angle is defined as an angle in a direction circumferential to the optical axis), allowing further selection of the compass angle using the LED drivers, as well as the azimuth angle selected by the LCDs and polarized reflector(s) as described above.

In some embodiments, banks of LEDs are organized such that different banks have different colors of light. In some such embodiments, an image is obtained at each of a plurality of colors, the quality of the images is determined by image processor 202, and the color (or combination of colors) that yields the best image is used.

In some embodiments, banks of LEDs are organized such that different banks have different dispersion angles light (e.g., using LEDs having different emission angles). In some such embodiments, an image is obtained at each of a plurality of dispersion angles, the quality of the images is determined by image processor 202, and the parameter that yields the best image is used.

In some embodiments, banks of LEDs are organized such that different banks have different colors of light. In some such embodiments, an image is obtained at each of a plurality of colors, the quality of the images is determined by image processor 202, and the color that yields the best image is used.

In other embodiments, each component of FIG. 1 is a straight plane extending into the drawing sheet, such that illumination source 106 includes two linear halves, each having a straight-line or plane light source 108, a plane polarizer 110, a plane liquid-crystal device (LCD) 112, a plane angled polarized reflector/transmitter 114, a second plane LCD 116, and a second plane angled polarized reflector/transmitter 114. In some embodiments, further pairs of LCDs and angled reflectors (shown as ellipses 120) are included. In some embodiments, for the outermost section, LCD 116 is omitted and reflector 118 reflects all incident light.

In yet other embodiments, each component of FIG. 1 is a straight plane section of a polygon centered about optical axis 105, such that illumination source 106 includes a plurality of sections, each having a straight-line or plane light source 108, a plane polarizer 110, a plane liquid-crystal device (LCD) 112, a plane angled polarized reflector/transmitter 114, a second plane LCD 116, and a second plane angled polarized reflector/transmitter 114. In some embodiments, further pairs of LCDs and angled reflectors (shown as ellipses 120) are included. In some embodiments, for the outermost section, LCD 116 is omitted and reflector 118 reflects all incident light.

Figure 2:
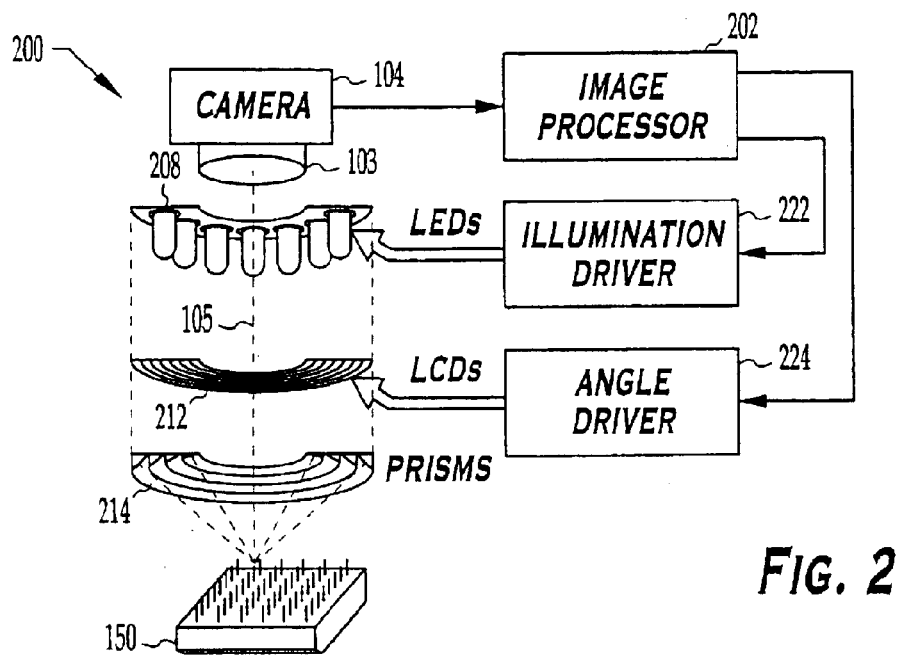
FIG. 2 shows a cut-away side-view schematic of another embodiment of the present invention, an electronically-controlled variable-angle machine-vision illumination system 200.

FIG. 2 shows a cut-away side-view schematic of another embodiment of the present invention, an electronically-controlled variable-angle machine-vision illumination system 200. In some embodiments, illumination system 200 includes a flat ring light source 208 having one or more concentric rows of LEDs, a flat ring liquid-crystal device 212, and a concentric angular refraction element 214 that includes concentric Fresnel groves concentric prisms, or a concentric hologram. The ring LCD 212 includes a plurality of separately drivable LCD ring patterns, each driven by LCD angle driver 224, such that one or more concentric rings is transparent to the light from light source 208, while other concentric rings of LCD 212 are opaque or reflective to the incident illumination. Thus, in some embodiments, each ring of prisms 214 (or Fresnel grooves or holographic deflectors rings) refracts the light incident to it at a different conical angle, and the rings of LCD 212 select which ring of prism 214 will get light. One or more of the concentric LCD rings of 212 are dedicated to each of the plurality of conical angles that may be illuminated, and one or more of the conical angles may be activated simultaneously. This allows angle driver 224 to select which azimuth angle or angles of illumination will be activated. In some embodiments, one or more concentric rings of LCD 212 will be driven to be in a substantially transparent state, and zero or more other rings of LCD 212 will be driven to be in a substantially reflective state, and the substrate of light source 208 (i.e., the surface under and around the LEDs) is made reflective, such that the light reflected by LCD rings in a reflective state has another chance to go through those ring sections that are transparent to be sent to device 150 at the desired angle(s).

In some embodiments, illumination driver 222 provides a short pulse of current to all the LEDs at once (e.g., providing a cone of illumination or illumination centered on one or more conical sections). In some embodiments, illumination driver 222 includes drivers such as described in U.S. patent application Ser. No. 09/349,684, entitled "MACHINE-VISION SYSTEMS AND METHODS WITH UP AND DOWN LIGHTS", filed Jul. 8, 1999, and/or U.S. Pat. No. 5,745,176 entitled MACHINE VISION ILLUMINATION SYSTEM AND METHOD" ISSUED Apr. 28, 1998 (both incorporated by reference). In some other embodiments, the LEDs of light source 208 are divided into banks, wherein each bank is separately driven by illumination driver 222 (e.g., eight banks, wherein each bank represents a forty-five-degree section of the ring, for example the eight compass directions N, NE, E, SE, S, SW, W, and NW), allowing further selection of the compass angle of illumination using the LED drivers, as well as the azimuth angle selected by the LCDs 212 and refractor ring(s) as described above.

Figure 3:
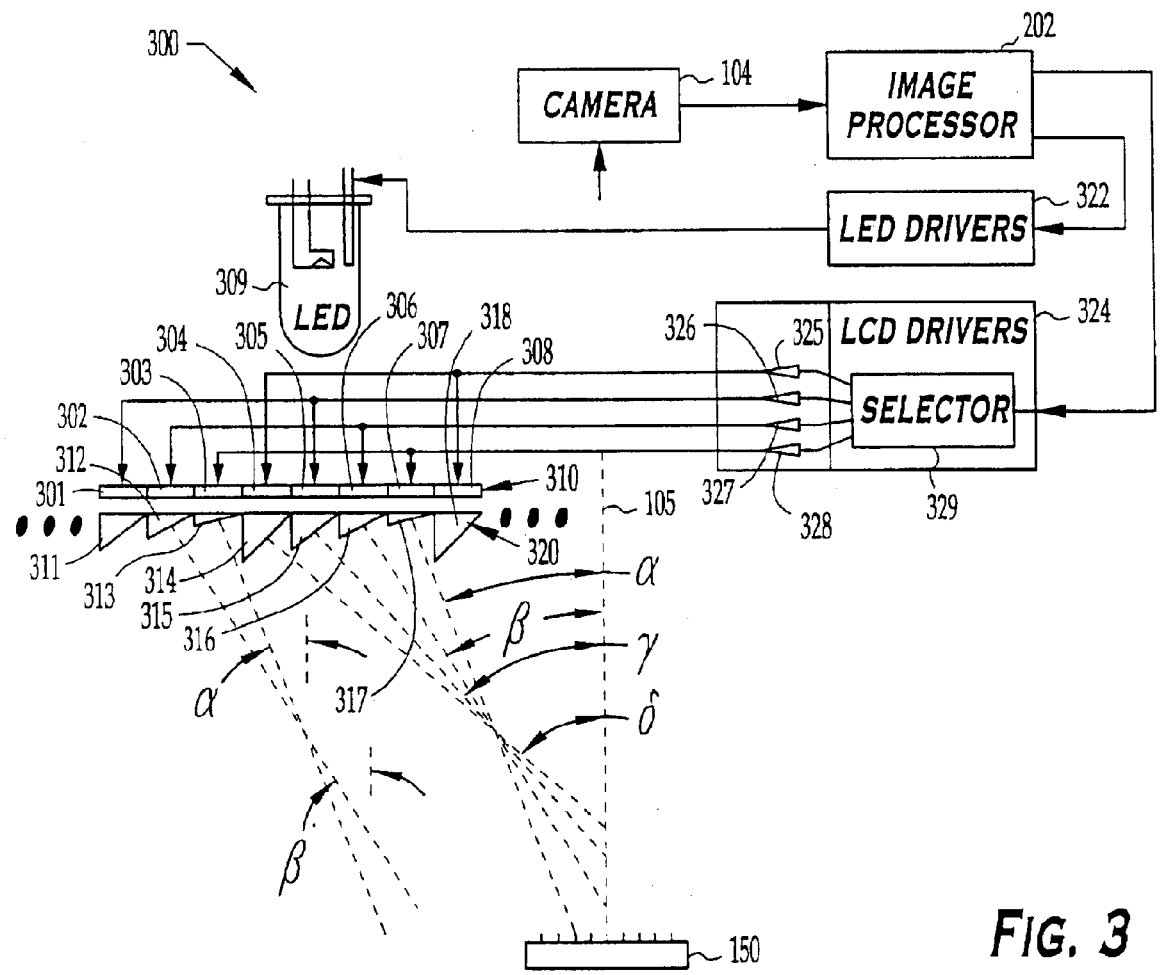
FIG. 3 shows a cut-away side-view schematic of yet another embodiment of the present invention, an electronically-controlled variable-angle machine-vision illumination system 300.

FIG. 3 shows a cut-away side-view schematic of yet another embodiment of the present invention, an electronically-controlled variable-angle machine-vision illumination system 300. In some embodiments, system 300 represents a detailed view of system 200 of FIG. 2. Thus, in these embodiments, LCDs 310 include a plurality of concentric ring LCD areas (shown are rings 301, 302, 303, 304, 305, 306, 307, and 308), each ring area driven by one of the drivers 324. In the embodiment shown, selector 329 selects one or more individual drivers 325, 326, 327, and/or 328. Driver 325 drives LCD ring sections 304 and 308; driver 326 drives LCD ring sections 301 and 305; driver 327 drives LCD ring sections 302 and 306; driver 328 drives LCD ring sections 303 and 307. In some embodiments, further concentric rings are added to each of these four sets. In other embodiments, more or fewer sets are provided, and more or fewer LCD areas are included in each set. Since LCD drivers 324 can drive one or more LCD sets, one or more angles selected from the four angles alpha, beta, gamma, and delta ($\alpha, \beta, \gamma,$ and $\delta$) can be illuminated at one time. In embodiments that are circularly symmetric, these are conical angles to the optical axis 105. In some embodiments, LED drivers 322 drive LED light source 309 in one or more banks, as described above for illumination driver 222 of FIG. 2

In other embodiments, FIG. 3 represents a linear (i.e., straight line) illumination source, one or more of which are implemented at selected compass angles around object 150 and optical axis 105. In some such embodiments light source 308 includes one or more rows of LEDs organized on one or more banks, similarly to the circular arrangement described above.

Figure 4:
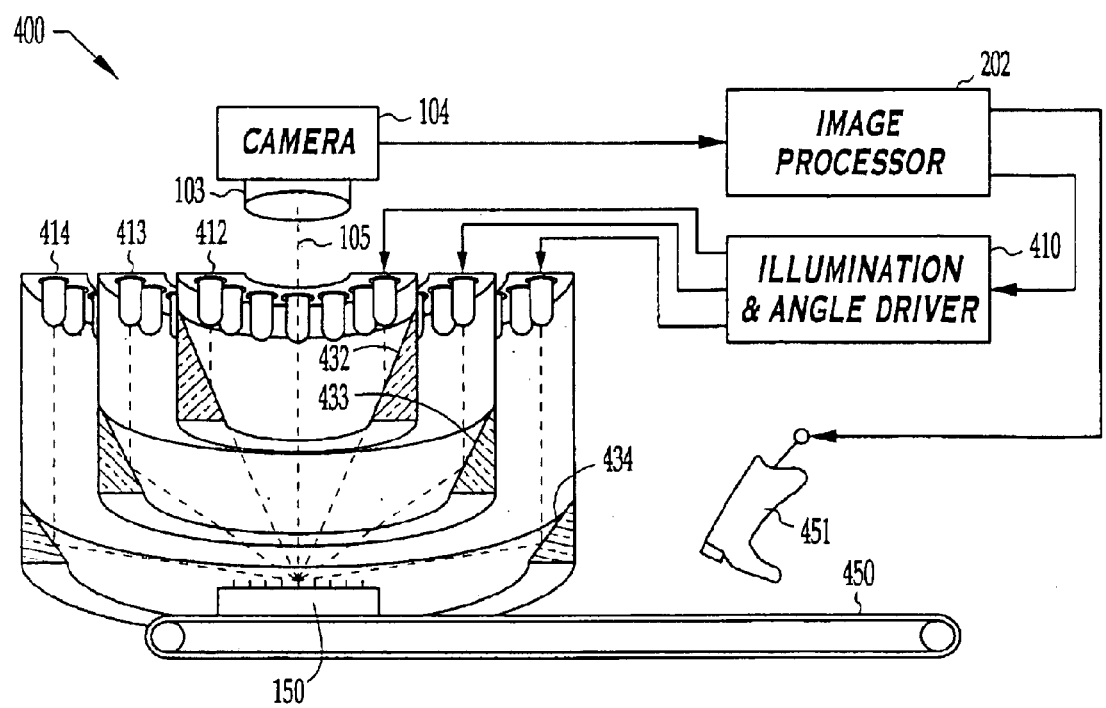
FIG. 4 shows a cut-away side-view schematic of yet another embodiment of the present invention, an electronically-controlled variable-angle machine-vision illumination system 400.

FIG. 4 shows a cut-away side-view schematic of yet another embodiment of the present invention, an electronically-controlled variable-angle machine-vision illumination system 400. In some embodiments, system 400 includes camera 104 that provides images to image processor 202, which drives illumination and angle driver 410 which drives concentric rings of LEDs 412, 413, and 414. In some embodiments, angled ring reflectors 432, 433, and 434 provide steep, medium, and shallow conical reflections angles respectively. Ring 412 includes one or more concentric rows of LEDs, and when activated by driver 410, provides a steep conical illumination to object 150 as reflected by reflector 432. Similarly, ring 413 includes one or more concentric rows of LEDs, and when activated by driver 410, provides a steep conical illumination to object 150 as reflected by reflector 433; and ring 414 includes one or more concentric rows of LEDs, and when activated by driver 410, provides a steep conical illumination to object 150 as reflected by reflector 434.

Some embodiments further include a support station 450 (such as a conveyor belt) that supports an object being inspected by the machine vision system, and a selector 451 that rejects that object based on an analysis of the image.

In some embodiments (not shown), a variable-angle liquid-crystal reflector, such as available from Boulder Nonlinear Systems Incorporated (BNS), a privately-held Colorado business located at 450 Courtney Way, #107 Lafayette, Colo. USA 80026, is used to provide electronically controlled beam reflection at various different angles. For example, in some embodiments, light from an array of LEDs is reflected off of an LCD reflective device such as a Boulder Nonlinear Systems Incorporated 1×4096 optical Beam Steering Array having 4096 pixels, and arranged as a reflective VLSI backplane in ceramic PGA carrier, and having an array size of 7.4×7.4 mm with a pixel size of 1 $\mu$m wide by 7.4 mm high and a pixel pitch of 1.8 $\mu$m. In some embodiments, a liquid crystalline mixture comprising nematic or chiral smectic liquid crystal active material is used. In some embodiments, this provides an optical modulation (analog) ~ 4 to 6 bits linear modulation levels providing a resolution of 225 different angles and steer angles of ±3.4° (with light wavelength $\lambda$=1550 nm), and random selection of steer angle. In other embodiments, a liquid crystal refractor of similar design is used to replace the variable-angle mechanism 310 and 320 of FIG. 3.

In various embodiments, image processor 202 of FIG. 2 or FIG. 3 or FIG. 4 obtains one or more images, each at a selected angle (conical angle and/or compass angle) of illumination, examines (e.g., using a computer program) one or more regions of interest to determine the quality of the image obtained, and based on a quality criterion, optionally changes the illumination angle(s) and obtains further images, in order to choose an illumination angle or angles that provide an acceptable image, such as described further below.

Figure 5:
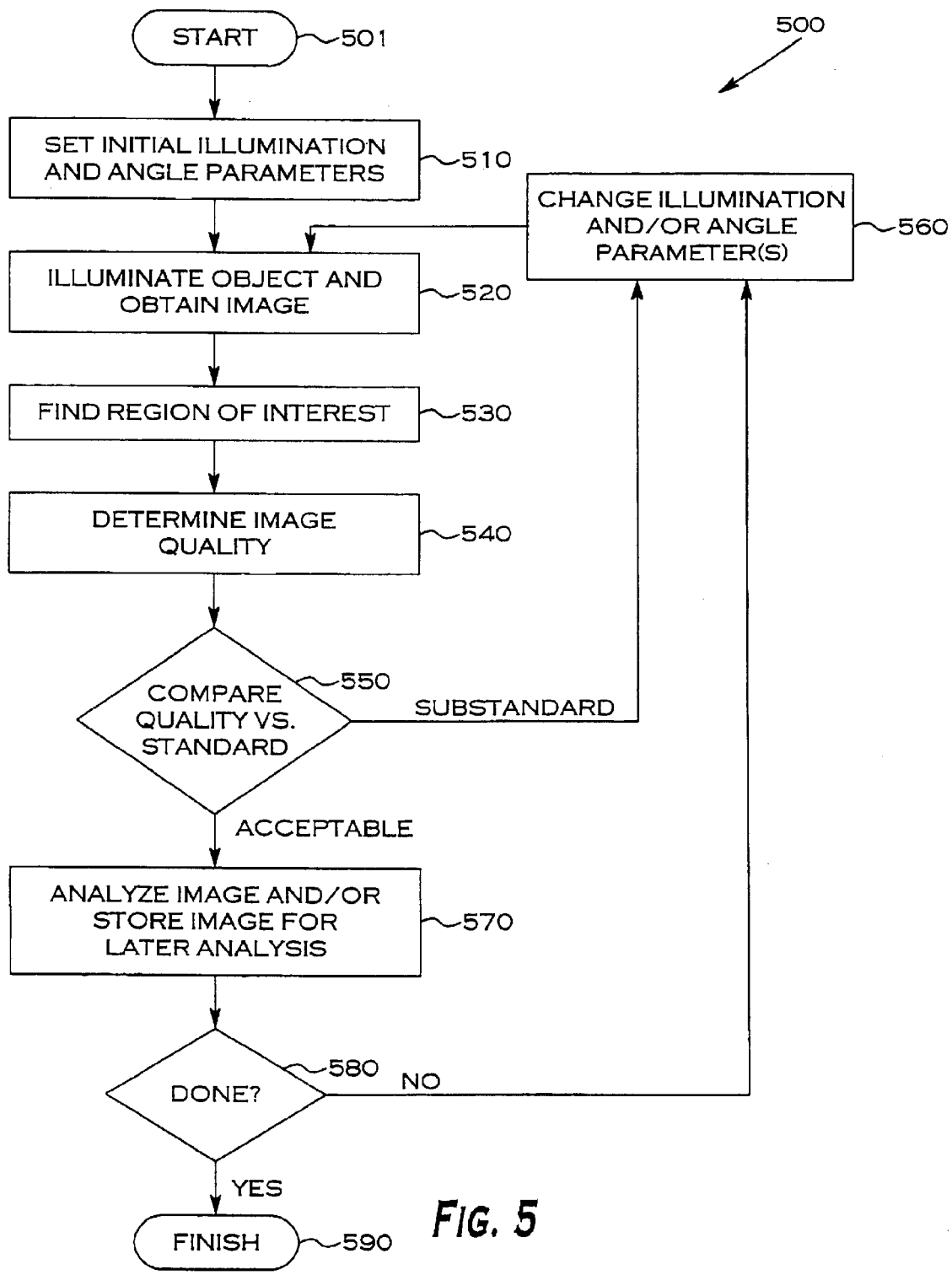
FIG. 5 shows a flowchart schematic of yet another embodiment of the present invention, an electronically-controlled variable-angle machine-vision illumination method 500.

FIG. 5 shows a flowchart schematic of yet another embodiment of the present invention, an electronically-controlled variable-angle machine-vision illumination method 500. In some embodiments, after start 501, block 510 sets initial illumination and angle parameters (e.g., processor 202 (see FIG. 2, 3, or 4) sets drive parameters to illumination driver 222, 322, or 410 and to angle drivers 224, 324, or 410, for example setting the LED pulse width and current amount, selecting which LEDs will be driven, and/or selecting which LCD areas or rings will be made transparent or polarization angles that are set). Control passes to block 520, where the object(s) 150 is/are illuminated, and an image is obtained (e.g., by imager 104). Control passes to block 530, where the region of interest in the image is located. Control passes to block 540, where the quality of the image within the region of interest is determined (e.g., the contrast amount on certain pins of a pin-grid-array electronic device is checked to generate a quality parameter). Control passes to block 550, where the quality parameter generated by block 540 is compared to a standard (e.g., to an absolute standard value for image quality, or relatively to quality parameters determined for other illumination angle(s), such as when multiple images are taken of an object 150 and compared one to the other(s) to determine which angle yields the "best" image). If, at block 550, it is determined that the image is substandard (relative to an absolute quality standard) or that more images are needed to compare one to the others, then control passes to block 560 where the illumination and/or angle parameter(s) are changed, and the imaging blocks (520–550) are iterated. Once one or more acceptable images are obtained using the various azimuth angle illumination and compass-angle illumination parameters, control passes to block 570, where the image obtained is analyzed and/or stored for further later analysis. Such machine-vision analysis is performed using any process well-known to those of skill in the art; and a determination is optionally made as to whether the quality of the object (e.g., manufactured part) is acceptable or not. If not acceptable, the part is rejected, and/or the manufacturing process is adjusted to generate more acceptable parts. In some embodiments, at block 580, a determination is made as to whether more images are needed (if we are not done, control passes to block 560 to again change the illumination parameters as iterate through the above process), and if we are done, control passes to the finish 590.

Other embodiments of the invention use a piezo-electric mechanism to vary the refractive properties of a ring lens, that is, a lens having a central hole or cutout. In this embodiment, the imager 104 peers through the hole in the ring lens to an object 150. Another embodiment uses a liquid-crystal panel to vary the angle of reflection of a ring reflector.

Conclusion

In some embodiments, the present invention provides a machine-vision system having an optical axis, including a processor; an imager coupled to the processor; means for emitting light; means for selective polarizing the light; and means for selectively reflecting the polarized light in a predetermined direction relative to the optical axis based on its polarization.

In some embodiments, the present invention provides a machine-vision system including a processor; an imager coupled to the processor; at least one light source; at least one liquid-crystal panel proximate the one light source; and at least one reflector proximate the one liquid-crystal panel.

In some embodiments, the present invention provides a machine-vision system including a processor, an imager coupled to the processor, at least one light source for emitting light, at least one liquid-crystal panel proximate the one light source for selectively changing polarization of the light, and at least one selective reflector proximate the one liquid-crystal panel for selectively reflecting light from the liquid-crystal panel based on its polarization.

In some embodiments, the present invention provides apparatus including means for emitting light, means for selective polarizing the light, and means for selectively reflecting the polarized light in a predetermined direction based on its polarization.

In some embodiments, the present invention provides a machine-vision system having an optical axis, including a light emitter having a polarization, and an electrically activatable polarized reflector unit for selectively reflecting the light in a predetermined direction relative to the optical axis based on its polarization.

In some embodiments, the present invention provides an illumination method including emitting light, selectively polarizing the light, and selectively reflecting the light based on its polarization.

In some embodiments, the present invention provides a machine-vision system having an optical axis, including a light source, means for selectively directing light in a first predetermined direction relative the optical axis based on its polarization, and means for selectively directing light in a second predetermined direction relative to the optical axis based on its polarization.

One aspect of the present invention provides a machine-vision system 100 having an optical axis 105. This system 100 includes a light source 108–110–112 emitting light having a polarization, a machine-vision imager 104 that obtains an image of an object illuminated by the light, a processor 102 coupled to receive an image from the imager, and operative to generate a quality parameter based on the image, and one or more of the various means as described above for selectively directing the light in a predetermined pattern based on its polarization and based on the quality parameter of the image.

In some embodiments, the means for selectively directing the light include a liquid-crystal device 112. In some embodiments, the means for selectively directing the light further include a polarized reflector 114.

Another aspect of the present invention provides a machine-vision system 100, 200, 300, or 400 having an optical axis 105. This system includes a machine-vision imager 104 located along the optical axis 105, a controllable light source (108–110–112, 208–212, 310, or 412–413–414), a first optical element (114, 214, 311, or 432) that selectively directs light in a first predetermined pattern relative to the optical axis based on light characteristics, a second optical element (118, 214, 312, or 433), that directs light in a second predetermined pattern relative to the optical axis, and an electronic controller 102 or 202) operatively coupled to the imager 104 and the controllable light source to control the light characteristics and thereby selecting one or more of the first and second predetermined patterns.

In some embodiments, the controllable light source includes a light source (108), and a controllable polarizer (111) for setting a polarity of the light, wherein the electronic controller is operatively coupled to the controllable polarizer to control the light polarization characteristics and thereby selecting one or more of the first and second predetermined patterns.

In some such embodiments, the first optical element 114 includes a polarized reflector that reflects light polarized on one direction and transmits light polarized in another direction.

In some embodiments, the controllable light source includes a light source 208, and a liquid crystal device (LCD) 212 having two or more areas that are each controllable to selectively transmit light.

In some embodiments, the first optical element includes a prism refractor 214 or 311 that refracts light in the first pattern when a first one of the two or more LCD areas transmits light.

In some embodiments, the second optical element includes a prism refractor 214 or 312 that refracts light in the second pattern when a second one of the two or more LCD areas transmits light.

In some embodiments, the controllable light source includes a light source 208 or 412–413–414 having two or more banks each having one or more LEDs and each operatively coupled to be activated by the electronic controller, wherein one or more of the banks can be simultaneously activated.

In some embodiments the first optical element is a ring reflector 432 situated to reflect only light from a first one of the banks 412, and the second optical element is a ring reflector 433 situated to reflect only light from a second one of the banks 413.

In some embodiments, the electronic controller 202 further selects a region of interest of an image, determines an image quality within the region of interest, and selectively controls the first and second light pattern based on the image quality.

Some embodiments further include a support station 450 (such as a conveyor belt) that supports an object being inspected by the machine vision system, and a selector 451 (see FIG. 4) that rejects that object based on an analysis of the image.

Another aspect of the present invention provides an illumination method that includes emitting light, selectively polarizing the light, and selectively directing the light based on its polarization (see FIGS. 1, 2, and 3 above).

In some embodiments, the selectively directing provides two or more different angles of illumination (e.g., alpha and/or beta). In some such embodiments, the angle is a conical angle of a ring illumination.

In some embodiments, the selectively directing includes selectively reflecting based on polarization. In some embodiments, the selectively polarizing includes electronically driving a liquid-crystal device. In some such embodiments, the selectively directing further includes blocking light of one polarization and refracting light of another polarization (see, e.g., FIG. 3).

Yet another aspect of the present invention provides a machine-vision method for inspecting an object. This method includes (a) setting one or more illumination parameters, (b) illuminating the object based on the one or more illumination parameters, (c) obtaining an image of the illuminated object, (d) generating a quality parameter based on an image quality of a predetermined region of interest in the image, and (e) iterating (b), (c), and (d) using a different illumination parameter.

In some embodiments of this method the iterating is based on the quality parameter. In some embodiments, the one or more illumination parameters includes a predetermined azimuth angle of illumination. In some embodiments, the one or more illumination parameters includes a predetermined compass angle of illumination. In some embodiments, the one or more illumination parameters includes a predetermined compass angle of illumination.

The embodiments described above are intended only to illustrate and teach one or more ways of practicing or implementing the present invention, not to restrict its breadth or scope. The actual scope of the invention, which embraces all ways of practicing or implementing the teachings of the invention, is defined only by the following claims and their equivalents.

What is claimed is:

1. A machine-vision system having an optical axis, comprising:
   a light source emitting light having a polarization;
   a machine-vision imager that obtains an image of an object illuminated by the light;
   a processor coupled to receive an image from the imager, and operative to generate a quality parameter based on the image; and
   means for selectively directing the light in a predetermined pattern based on its polarization and based on the quality parameter of the image.

2. The system of claim 1, wherein the means for selectively directing the light include a liquid-crystal device.

3. The system of claim 1, wherein the means for selectively directing the light further include a polarized reflector.

4. The system of claim 1, wherein the means for selectively directing the light include
   means for selectively polarizing the light; and
   means for selectively directing the light based on its polarization.

5. The system of claim 1, wherein the means for selectively directing provides two or more different angles of illumination.

6. The system of claim 1, wherein the means for selectively directing includes means for selectively reflecting based on polarization.

7. The system of claim 1, wherein the means for selectively polarizing includes means for electronically driving a liquid-crystal device.

8. The system of claim 1, wherein the means for selectively directing further includes means for blocking light of one polarization and refracting light of another polarization.

9. The system of claim 1, wherein the light director include a liquid-crystal device.

10. The system of claim 1, wherein the light director further include a polarized reflector.

11. A machine-vision system having an optical axis, comprising:
    a machine-vision imager located along the optical axis;
    a controllable light source;
    a first optical element that selectively directs light in a first predetermined pattern relative to the optical axis based on light characteristics;
    a second optical element that directs light in a second predetermined pattern relative to the optical axis; and
    an electronic controller operatively coupled to the imager and the controllable light source to control the light characteristics and thereby selecting one or more of the first and second predetermined patterns.

12. The system of claim 11, wherein the controllable light source comprises:
    a light source;
    a controllable polarizer for setting a polarity of the light, wherein the electronic controller is operatively coupled to the controllable polarizer to control the light polarization characteristics and thereby selecting one or more of the first and second predetermined patterns.

13. The system of claim 12, wherein the first optical element includes a polarized reflector that reflects light polarized on one direction and transmits light polarized in another direction.

14. The system of claim 11, wherein the controllable light source comprises:
    a light source;
    a liquid crystal device (LCD) having two or more areas that are each controllable to selectively transmit light.

15. The system of claim 14, wherein the first optical element includes a prism refractor that refracts light in the first pattern when a first one of the two or more LCD areas transmits light.

16. The system of claim 15, wherein the second optical element includes a prism refractor that refracts light in the second pattern when a second one of the two or more LCD areas transmits light.

17. The system of claim 11, wherein the controllable light source comprises:
    a light source having two or more banks each having one or more LEDs and each operatively coupled to be activated by the electronic controller, wherein one or more of the banks can be simultaneously activated.

18. The system of claim 17, wherein
    the first optical element is a ring reflector situated to reflect only light from a first one of the banks; and
    the second optical element is a ring reflector situated to reflect only light from a second one of the banks.

19. The system of claim 17, wherein the electronic controller further selects a region of interest of an image, determines an image quality within the region of interest, and selectively controls the first and second light pattern based on the image quality.

20. The system of claim 11, further comprising:
    a support station that supports an object being inspected by the machine vision system; and
    a selector that rejects that object based on an analysis of the image.

21. A machine-vision system having an optical axis, comprising:

a light source emitting light having a polarization;

a machine-vision imager that obtains an image of an object illuminated by the light;

a processor coupled to receive an image from the imager, and operative to generate a quality parameter based on the image; and a light director operatively controlled by the processor that selectively directs the light in a predetermined pattern based on its polarization and based on the quality parameter of the image.

\* \* \* \* \*